(12) United States Patent
Muenker

(10) Patent No.: US 8,437,447 B2
(45) Date of Patent: May 7, 2013

(54) LAMINOGRAPHY SYSTEM

(75) Inventor: Martin Muenker, Gevelsberg (DE)

(73) Assignee: YXLON International GmbH, Hamburg (DE)

( * ) Notice: Subject to any disclaimer, the term of this patent is extended or adjusted under 35 U.S.C. 154(b) by 262 days.

(21) Appl. No.: 13/041,487

(22) Filed: Mar. 7, 2011

(65) Prior Publication Data

US 2011/0222650 A1    Sep. 15, 2011

(30) Foreign Application Priority Data

Mar. 9, 2010    (DE) .................. 10 2010 010 723

(51) Int. Cl.
*A61B 6/00*    (2006.01)
(52) U.S. Cl.
USPC ............................................ 378/21
(58) Field of Classification Search .......... 378/11, 378/20–27, 57, 193, 195, 208
See application file for complete search history.

(56) References Cited

U.S. PATENT DOCUMENTS

| | | | |
|---|---|---|---|
| 4,211,927 A | 7/1980 | Hellstrom et al. | 378/26 |
| 4,926,452 A | 5/1990 | Baker et al. | 378/22 |
| 6,104,776 A | 8/2000 | Oikawa | 378/22 |
| 6,501,823 B1 | 12/2002 | Kim et al. | 378/22 |

FOREIGN PATENT DOCUMENTS

| | | |
|---|---|---|
| DE | 42 12 537 A1 | 10/1992 |
| DE | 38 54 865 T2 | 6/1996 |
| DE | 102 07 331 A1 | 1/2003 |
| FR | 2 538 114 A1 | 6/1984 |

*Primary Examiner* — Courtney Thomas
(74) *Attorney, Agent, or Firm* — Leydig, Voit & Mayer, Ltd.

(57) ABSTRACT

A laminography system includes a first linear guide defining a z-direction of a Cartesian coordinate system and an imaging radiation source fixable to the first linear guide and movable along the first linear guide. The radiation source is configured to form a cone of rays including a central ray defining a y-axis of the Cartesian coordinate system. A detector is disposed in a position so as to be struck at a center thereof by the central ray of the radiation source substantially in an x-direction of the Cartesian coordinate system. The system also includes a first rotation device configured to rotate the detector about a first axis of rotation that is parallel to a z-axis of the Cartesian coordinate system and that passes through an intersection of the central array and the detector. The detector is fixable to a second linear guide and is movable on the second linear guide along the first axis of rotation. An object slide is disposed between the radiation source and the detector. The object slide is configured to receive an object for inspection and is rotatable by a second rotation device about a second axis of rotation that is parallel to the first axis of rotation and that passes through an intersection of the central ray and the object for inspection.

12 Claims, 4 Drawing Sheets

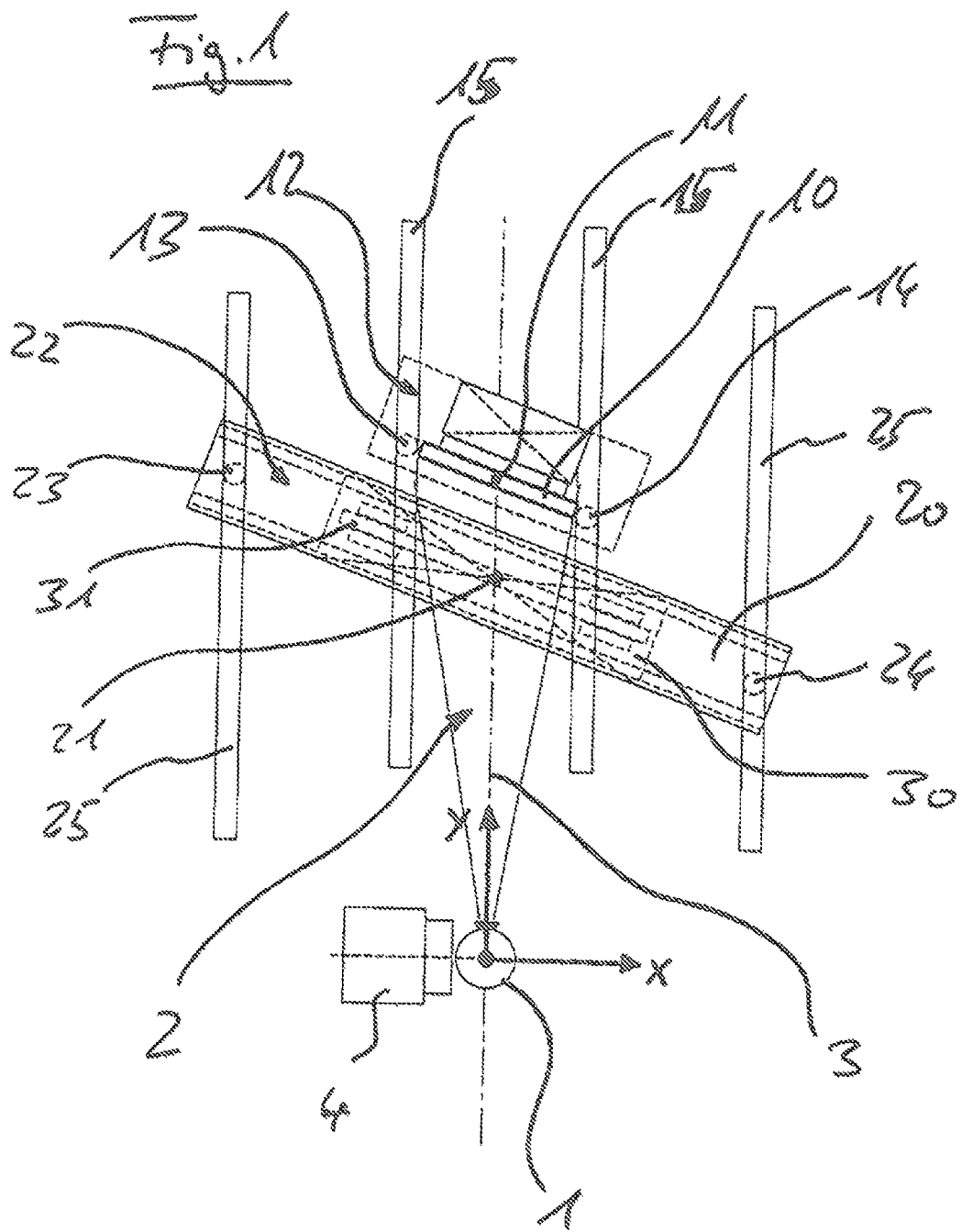

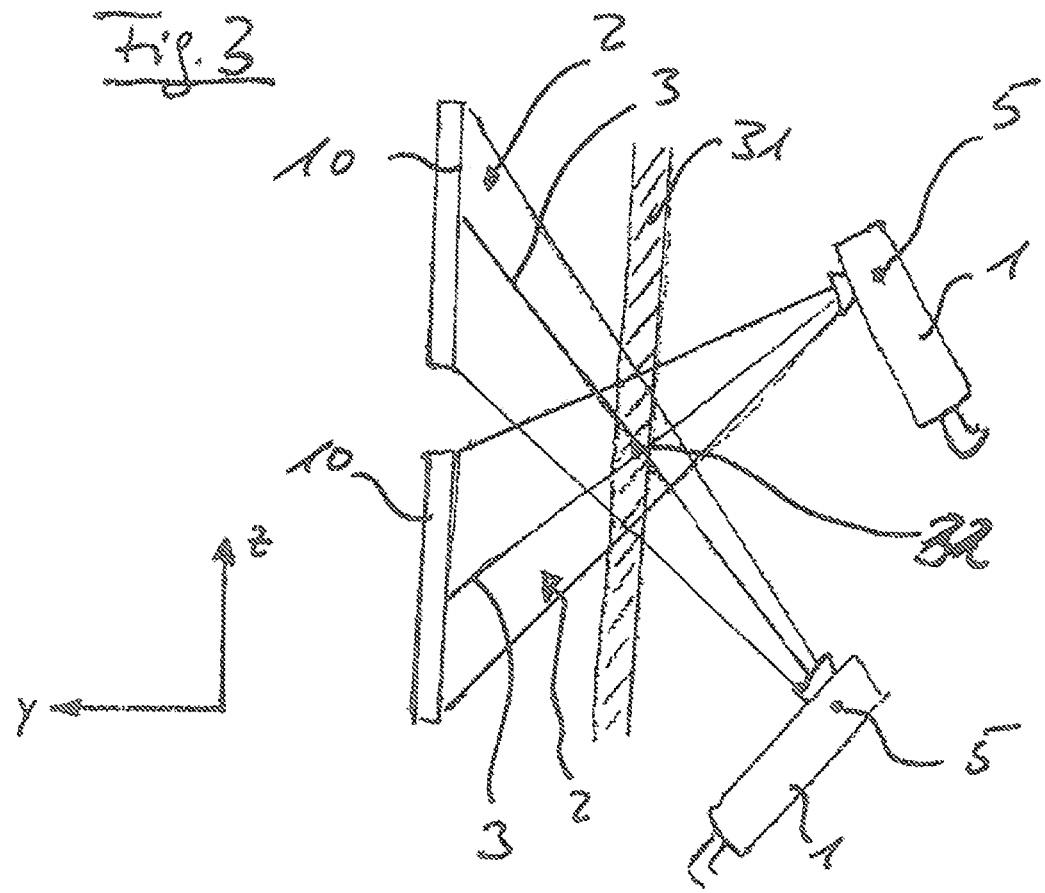

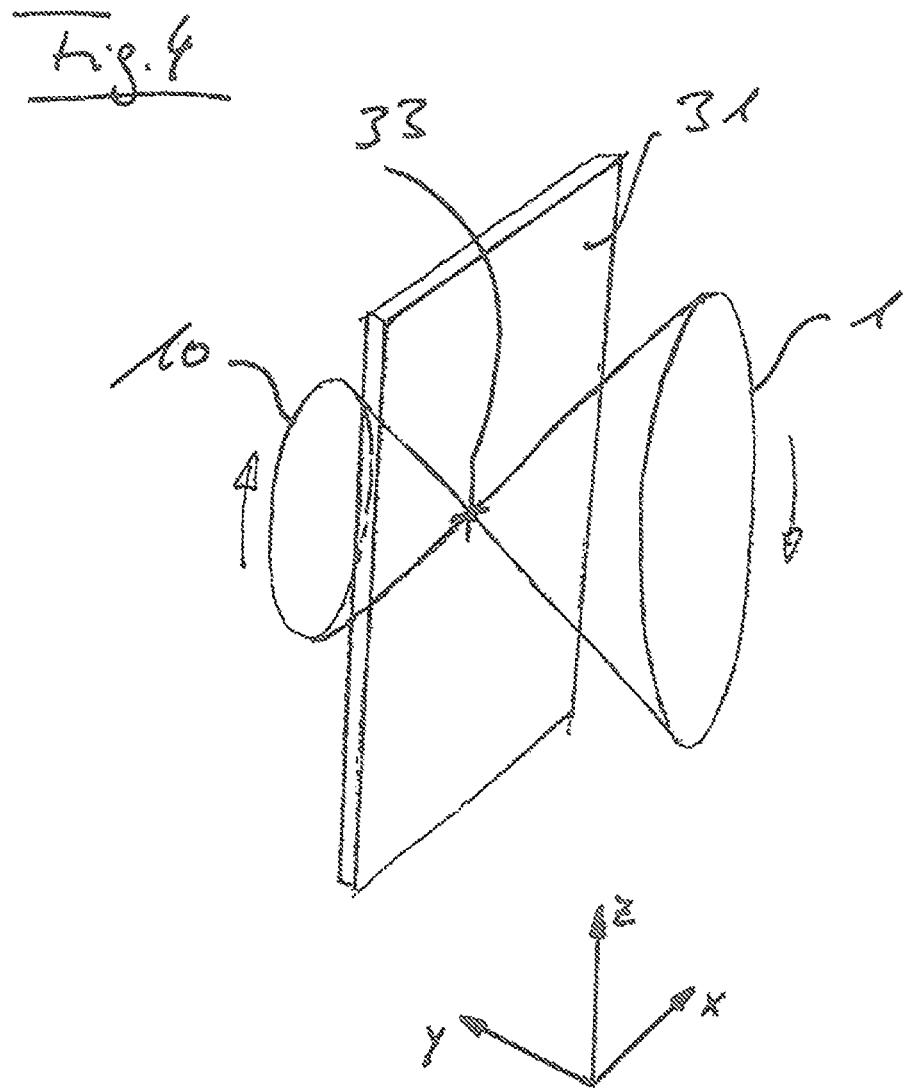

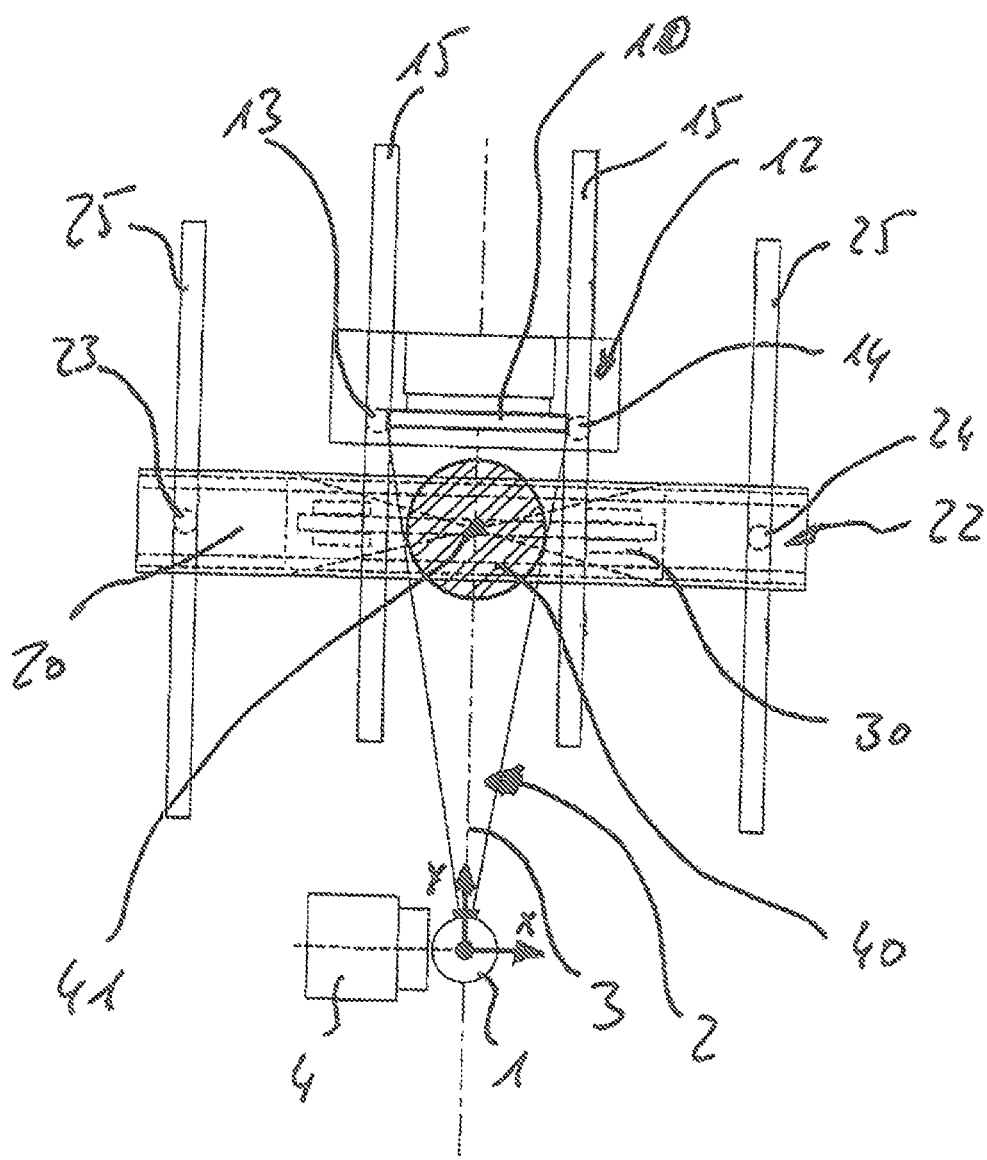

LAMINOGRAPHY SYSTEM

CROSS REFERENCE TO RELATED APPLICATIONS

This application claims priority to German Patent Application No. DE 10 2010 010 723.9, filed Mar. 9, 2010, which is hereby incorporated by reference herein in its entirety.

FIELD

The invention relates to a laminography system with a radiation source, a radiation detector and a movement and positioning device.

BACKGROUND

Digital laminography is used to inspect predominantly flat objects—where the extension in two directions is very great compared with the extension in the third direction—with a view to the 3-dimensional capture of a desired or undesired internal structure. It is used when simple radiography (direct or oblique radiography) does not allow an adequate representation of the 3D structure and other representation techniques, e.g. computed tomography, cannot be used. Laminography represents a further development of multi-angle radiography, comparable results are generated with limited angle CT, a special type of computed tomography, wherein the nature of the image reconstruction, i.e. the allocation of the individual projections to the volume imaging, differs.

Laminography systems are known from the state of the art. An overview of different designs of laminography systems can be found in DE 38 54 865 T2. A design is represented in U.S. Pat. No. 4,211,927 in connection with the properties of the imaging components, wherein the positioning is limited to a linear movement. Image acquisition in the case of digital laminography uses a synchronized, contrary movement or positioning of radiation source and detector relative to the object. The method is called linear laminography in the case of a linear movement and rotational laminography in the case of a movement on circular paths.

The movement occurs, in the case of both linear and rotational laminography, precisely about a virtual reference point, most often positioned in the object to be inspected, the movement plane is usually parallel to the surface of the object. The radiographic angle is defined, in conjunction with the distances between focus and object and between object and detector, by the length of displacement in the case of linear laminography and by the radius of the circular movement in the case of rotational laminography. This decisively influences the depth resolution in the radiation direction, thus the image quality and the detail recognition in the reconstructed laminograms.

In the case of linear laminography, because of the linear movement and the fluoroscopic images to be obtained thereby, only those structures that are not, or not nearly oriented in the plane defined by the direction of movement and the radiation direction—thus most often errors—can be captured in three dimensions. The more the orientation of the structure deviates from this named plane, the more spatial information the image contains. For the complete examination of the predominantly flat objects, a rotational laminography is therefore preferably carried out.

In the case of the known systems for carrying out linear or rotational laminography with moving imaging components, there are clear limitations both in respect of the method (path determined by the system geometry) and because of the rigidity and precision requirements to be met by the mechanical support structure, all the more so as the size and weight of the objects and/or the imaging components increase.

A decisive criterion for the image quality and (spatial) resolution is that the geometry of the imaging system is determined exactly, both in itself and in relation to the object for examination. Radiation source and detector are therefore usually coupled in a mechanical unit, the so-called C bend. If the object for examination is then rotated in the image plane in order to set the different irradiation directions in a plane lying parallel to the object, a rotational laminography data set is produced. If the C bend moves about a point of rotation lying in the object in a plane perpendicular to the object, a data set for limited angle CT is generated.

The dimensions and the bearing load of the C bend are to be matched to the object to be inspected and the components of the imaging system. As size and load increase, this problem can only be solved with substantial outlay. In addition, because of the optimized rigidity of the C bend, an alteration of the distance between focus and detector in order to change the magnification is to be realized only with high outlay. Many systems are therefore limited beforehand to a circular arc-shaped movement with a reference axis of rotation lying in the object. If a system which realizes a rotational laminography with a reference axis perpendicular to the object without rotation of the object is to be realized, the C bend must be cardanically suspended.

None of the known laminography systems allows travel along freely defined paths in the space (e.g. as any combination of linear and rotary movements), in particular not accompanied by an alteration—even simultaneous—of the distance between focus and detector (e.g. to travel along a path laid on a universal ball joint).

A further disadvantage especially of the X-ray rotational laminography systems available hitherto on the market which have no generators co-rotating with the radiation source is that an ad hoc critical or life-limiting twisting of the high-voltage cable results. This is the case in particular when large circle radii are to be travelled. In this case, it is as a rule necessary that the cone of rays of the radiation source is repositioned through a tilting, in order that the detector is still illuminated. The forces to be absorbed during such a twisting also limit the achievable mechanical precision.

A further limitation in rotational laminography systems produced according to known designs for high-power radiation sources, for example linear accelerators, is that on the one hand they cannot be operated in all directions and on the other hand, because of their size and their weight, they can be co-moved in a (in particular cardanically suspended) C arm on complicated, three-dimensional paths only with substantial outlay.

SUMMARY

It is therefore an aspect of the invention to provide a laminography system which allows a more flexible use of high-power radiation sources for laminography.

In an embodiment, the present invention provides a laminography system includes a first linear guide defining a z-direction of a Cartesian coordinate system and an imaging radiation source fixable to the first linear guide and movable along the first linear guide. The radiation source is configured to form a cone of rays including a central ray defining a y-axis of the Cartesian coordinate system. A detector is disposed in a position so as to be struck at a center thereof by the central ray of the radiation source substantially in an x-direction of the Cartesian coordinate system. The system also includes a first rotation device configured to rotate the detector about a first axis of rotation that is parallel to a z-axis of the Cartesian coordinate system and that passes through an intersection of the central array and the detector. The detector is fixable to a second linear guide and is movable on the second linear guide along the first axis of rotation. An object slide is disposed between the radiation source and the detector. The object slide is configured to receive an object for inspection and is rotatable by a second rotation device about a second axis of rotation that is parallel to the first axis of rotation and that passes through an intersection of the central ray and the object for inspection.

BRIEF DESCRIPTION OF THE DRAWINGS

Exemplary embodiments of the present invention are described in more detail below with reference to the drawings, in which:

FIG. 1 shows an embodiment of a laminography system while a rotational laminography is being carried out, FIG. 2 shows a schematic diagram of two extreme positions of a radiation source relative to a detector of a known system for carrying out a linear laminography;

FIG. 3 is a schematic diagram of the two extreme positions of a radiation source relative to a detector in a known system for carrying out a rotational laminography in a plane perpendicular to the representation in FIG. 2;

FIG. 4 is a schematic representation of the movements between a radiation source, detector and object to be inspected in the case of standard rotational laminography; and FIG. 5 is another embodiment of the invention for carrying out a computed tomography.

DETAILED DESCRIPTION

The following are considered as possible exemplary imaging radiation sources according to the invention: X-ray, gamma, neutron, light sources in the visible and invisible range, THz emitters and radar transmitters.

Within the framework of this application, to describe the alignment of the constituents of the rotational laminography system according to the invention, a Cartesian coordinate system related to the system is defined as follows:

The focus of the radiation source forms the origin of the coordinates; the y-axis runs along the central ray of the cone of rays emitted by the radiation source in the basic position of the radiation source in which this is not pivoted about a pivoting axis passing through the focus; the z-axis runs parallel to the direction of movement of the first linear guide of the radiation source; the x-axis is perpendicular to the plane defined by y-axis and z-axis.

This coordinate system can be oriented as desired vis-à-vis the universal coordinate system, i.e. the radiation direction can in principle be chosen freely and specific to the system.

In an embodiment of the invention, advantageously, for rotational laminography, the two contrary rotations of detector and radiation source are resolved in two pivoting movements perpendicular to each other (in the manner of a sine/cosine projection).

The radiation source is moved along the z-direction and the cone of rays is repositioned as needed by pivoting about a pivoting axis lying perpendicular to the axis of movement.

A further movement of the radiation source in a direction running perpendicular to it is not necessary according to the invention, as the circular contrary movements between radiation source and detector are achieved by having both the detector and the object slide (on which the object to be examined is arranged during the examination) carry out, synchronized with each other, the movement described below.

The detector can be moved in z-direction—in an opposite direction to the radiation source—in order that a relative movement for the linear laminography is realized.

In addition, the detector can be rotated about an axis of rotation running parallel to the first direction of movement. If a rotation of the object slide about the second axis of rotation which is formed parallel to the first axis of rotation of the detector is carried out synchronously with the rotational movement of the detector, this looks, from the reference point in the object, like an apparently synchronous circular movement of radiation source and detector about the reference point in planes lying on both sides of the object and parallel to the object. Thus, it is precisely not necessary to move the radiation source in a direction perpendicular to the z-direction. Because the dimensions and geometric relationships between radiation source, object slide and detector are known, on the one hand the movements which then correspond to a contrary rotational movement of radiation source relative to detector, in the case of a fixed object slide, can be calculated in advance without trouble dependent on each other, and on the other hand they allow the correction of the image distortion that results from the cone beam geometry and the changing geometric enlargement. As a result, it is thus not necessary to carry out the highly complex movements which were required with known rotational laminography systems. Rather, it suffices if the detector can be moved about this axis with a linear drive parallel to that of the radiation source and in addition to a rotational drive; and the object slide has a rotational drive which has a rotation device also operating parallel to the direction of movement of the radiation source.

In particular, the rotation devices can be formed very simply, as described further below as an advantageous development of the invention. With such an X-ray laminography system according to the invention, a twisting of the high-voltage cable does not occur, because the movement of the radiation source is linear only. In addition, a linear laminography can also be carried out with such an X-ray laminography system according to the invention. All that is required for this is a contrary movement by the two linear drives of the radiation source and the detector. The rotational drives for the detector and for the object slide are not active in this case. If the lengths of displacement are long, the tilting—thus the repositioning—of the cone of rays of the radiation source is also not a mechanical problem for the high-voltage cable.

A linear laminography can be realized perpendicular to the direction just described without modifying the device, by carrying out a synchronous, parallel rotation using the two rotation devices of the detector and object slide. During this movement corresponding to a parallel displacement, unlike with conventional displacement, the distance from radiation source to detector remains constant, which is to be borne in mind during the reconstruction.

An advantageous development of the invention provides that arranged on the object slide is an object holder which can be moved relative to this in x-direction, with reference to the alignment of the object slide in the xz-plane, and can be fixed to this. It is thereby possible not only to inspect a single line, but to move the object to be inspected in x-direction through the displacement of the object holder on the object slide. In combination with the z-movement of radiation source and detector, a surface of the object can thereby be inspected, without the need to remove the object from the object slide or shift it by hand on the object slide itself.

A further advantageous development of the invention provides that the detector can be moved in y-direction by means of a first translation device and/or the object slide can be moved in y-direction by means of a second translation device and can be fixed. It is thereby possible to alter the distance between radiation source and detector as well as between radiation source and object. This means that the magnification or other imaging properties can be altered. The X-ray laminography system according to the invention can thus be used even more generally.

A further advantageous development of the invention provides that the first rotation device has two drive points, first and second, which can be moved linearly independently of each other in y-direction and which are moved via a first and a second drive device which can be controlled independently of each other. It is thereby not necessary to provide a rotation device which carries out a rotational movement, this being replaced instead by contrary movements of the two linear drive devices, which leads to a simplification of the design. The same applies with regard to the second rotation device if there are two drive points, third and fourth, which can be moved linearly independently of each other in y-direction and which are moved via a third and fourth drive device which can be controlled independently of each other.

A further advantageous development of the invention provides that the radiation source has a pivoting axis which runs in the x-direction of the Cartesian coordinate system through the focus of the radiation source. The repositioning, already mentioned above, of the cone of rays which is desirable when the lengths of displacement are long is thereby made possible, in order to continue to illuminate the detector and obtain informative results. For short lengths of displacement or where the angles of radiation are large, however, this feature is not essential.

A further advantageous development of the invention provides that arranged on the object slide or on the object holder is a rotary plate, the axis of rotation of which is aligned in z-direction and which is driven by a CT-capable rotation device. It is thereby possible that a computed tomography can also be carried out with the X-ray laminography system. The object to be inspected is then fixed on the rotary plate. Should it be necessary—the object to be examined thus projects sideways from the cone of rays—the measurement circle can be extended horizontally through a lateral movement of the object with a simultaneous tilting of the detector (thus a rotation about the first axis of rotation). A transverse movement of the detector is not necessary. A vertical extension of the measurement circle can also be achieved by the X-ray laminography system according to the invention by moving the detector along the first axis of rotation on the second linear guide; if desired, the radiation source can be repositioned along the first axis of rotation by a linear movement. A computed tomography can thus be carried out by simple movements.

A further advantageous development of the invention provides that the first translation device coincides with the first rotation device and/or the second translation device coincides with the second rotation device. The structure of the X-ray laminography system is thereby simplified, as the same device can be used for the translational movement in y-direction (which is used to change the magnification for example) as that with which the rotation of the detector or object slide is also carried out, as this rotation device is realized by two linear drives.

It is preferred that the radiation source is an X-ray source and the detector is an X-ray sensitive detector. With an X-ray laminography system according to the invention, expanded measurement modes, for example elliptical or wholly free paths, can also be generated via corresponding control of the linear drives and rotational drives. On the basis of the already existing practical application of the laminography method, the application is described using X-ray laminography. Device and method can, however, also be used for other imaging radiation sources (e.g. gamma or neutron sources, light sources in the visible and invisible range, THz emitters, radar transmitters) and the associated radiation detectors.

A first embodiment of an X-ray laminography system according to the invention is represented in FIG. 1, with which a linear laminography, a rotational laminography or a limited angle CT can be carried out. In addition, with this system it is also possible, within the movement limits of the linear and rotational axes, to travel along any type of path, flat or three-dimensional, within the framework of a modified laminography method.

Before the embodiment of the X-ray laminography system according to the invention according to FIG. 1 is explained in more detail, the principle of a linear laminography is explained using FIG. 2, wherein the reference numbers used in the embodiment example according to the invention of FIG. 1 have been adopted. An object 31 to be examined is arranged, fixed, between a radiation source 1 and a detector 10. The detector 10 is moved parallel to the x-axis (illustrated by the arrow) linearly between the two extreme positions represented. In the opposite direction (also illustrated by an arrow), the radiation source 1 is also moved parallel to the x-axis such that its cone of rays 2 always illuminates the detector 10 in full. For this, it is typical that the radiation source 1 changes its direction of radiation. This is achieved by rotating the radiation source 1 about an axis which is aligned parallel to the z-axis and preferably runs through the focal point of the radiation source 1. The contrary movements of radiation source 1 and detector 10 are matched to each other such that the central ray 3 of the radiation source 1 always passes through a previously defined point within the object 31. An axis parallel to the z-axis through this point thus forms a virtual second axis of rotation 21. With such a system, the object 31 can be inspected along a line parallel to the z-axis, thus along the second axis of rotation 21.

If an inspection of the object 31 not limited to the error direction is to be carried out, this is possible by means of a rotational laminography. The matched synchronous circular movement of radiation source 1 relative to detector 10 represented in FIG. 4 is divided in FIGS. 2 and 3 into two partial movements perpendicular to each other.

As mentioned at the beginning, the system-based coordinate system can be oriented as desired vis-à-vis the universal system, but not all radiation sources 1 are to be operated in any orientation. A combined tilting and rotating movement is desired, which requires a substantial outlay on machinery in particular in the case of large and heavy radiation sources 1. These problems can be solved or their effect limited with the reduction according to the invention of the degrees of freedom of the movement of the radiation source 1.

In the superimposition of the two partial movements, it also becomes clear that the repositioning of the cone of rays 2 in z-direction results in a noncritical dragging movement (FIG. 3), but in the case of the movement perpendicular to it results in a twisting of the high-voltage cable (FIG. 2).

The advantage of the embodiment according to the invention represented in FIG. 1 is based, primarily, on the fact that the radiation source 1 is displaced only along the z-axis and there is a repositioning about the pivoting axis 5 which runs parallel to the x-axis (see FIG. 3).

To carry out the linear movement of the radiation source 1 along the z-axis, this is connected to a first linear guide 4. This movement is carried out to position the radiation source 1 opposite the central point of the examination area, in the case of a translational laminography oriented in z-direction or when carrying out a rotational laminography.

The transverse and rotational movement represented in FIG. 2 is replaced by the coordinated rotation of object 31 and detector 10 (see FIG. 1).

The detector 10 is arranged on a first translation device 12 which has two drive points independent of each other, a first drive point 13 and a second drive point 14. These two drive points 13, 14 are each guided in a guide, both running parallel to the y-axis. Upon a synchronous movement of the two drive points 13, 14, a translational movement of the detector 10 away from or towards the radiation source 1 thus occurs. In the case of a non-synchronous or contrary movement of the two drive points 13, 14, on the other hand, there is a rotation of the detector about a first axis of rotation 11 which runs parallel to the z-axis within the detector 10—optionally in conjunction with a translation in y-direction.

In addition, the detector 10 is also connected to a second linear guide by which this can be moved parallel to the z-axis. This is comparable to the first linear guide 4 of the radiation source 1. This second linear guide is—like the first linear guide 4 of the radiation source 1—used for the basic positioning of the system, for the translational laminography oriented in z-direction and the rotational laminography.

The alignment of radiation source 1 relative to detector 10 is such that the cone of rays 2 illuminates the detector 10 in full in any position. Furthermore, the central ray 3 of the cone of rays 2 passes through the first axis of rotation 11 of the detector 10. To carry out a rotational laminography with high displacement paths, the radiation source 1 can also be pivoted about the x-axis (corresponds to the pivoting axis 5 in FIG. 3), in order to constantly be able to fully illuminate the detector 10 which is moved in the opposite direction relative to the radiation source 1 along the z-axis.

The object 31 is arranged on an object slide 20 which comprises a second translation device 22 which is designed substantially the same as the first translation device 12 of the detector 10. It has two drive points which can be moved independently of each other, the third drive point 23 and the fourth drive point 24. These two drive points 23, 24 are each guided in a guide 25, both running parallel to the y-axis and thus also parallel to the guides 15 of the detector 10. It is expedient to arrange the two guides 25 of the object slide 20 outside the two guides 15 of the detector 10, as the object slide 20 is as a rule wider than the detector 10 and thus all drive points 13, 14, 23, 24 can be arranged in the respective outer end area of the first translation device 12 and the object slide 20. On the basis of the named second translation device 22, in principle the same movements are possible as have already been described above for the detector 10, thus a translational movement along the y-axis and/or a rotation about the second axis of rotation 21 (already described above for FIG. 2) which is located within the object 31.

The object 31 is not arranged directly on the object slide 20, but on an object holder 30 which can be moved on the object slide 20 and can be fixed to it in predetermined positions. The direction of movement is parallel to the connecting line between third drive point 23 and fourth drive point 24. Different second axes of rotation 21 which are relevant for the area to be inspected of the object 31 can thus be set without the object 31 having to be removed from the object holder 30 and reinserted elsewhere.

Because of the respectively possible translational movement of both the detector 10 and the object 31 along the y-axis—wherein these translational movements can be independent of each other—different distances can be set both between radiation source 1 and detector 10 and between object 31 and detector 10. It is thereby possible to set different image geometries, in particular with different degrees of magnification, and thus to respond individually to the image geometry depending on the object 31 to be inspected and the radiation source 1 used or the detector 10 used.

To carry out a linear laminography oriented in x-direction, detector 10 and object slide 20 are rotated synchronously with each other about the first axis of rotation 11 (applies to the detector 10) or the second axis of rotation 21 (applies to the object slide 20). For this, the first translation device 12 and the second translation device 22 respectively are moved synchronously with each other by moving the respective drive points 13, 14; 23, 24 synchronously. These movements thus replace the contrary movement of radiation source 1 and detector 10 represented in FIG. 2 when object 31 (or object slide 20) is fixed. In this case it is also advantageous that, even if the lengths of displacement are long, no repositioning of the radiation source 1 about an axis parallel to the z-axis—as represented in FIG. 2—is necessary, as the long length of displacement is replaced by a stronger rotation of the detector 10 about the first axis of rotation 11 and the complete illumination of the detector 10 by the cone of rays 2 of the radiation source 1 is thus guaranteed even in these extreme positions.

Carrying out a rotational laminography or a laminography on a freely choosable path uses a more complicated contrary movement of the radiation source 1 and detector 10 along the first linear guide 4 of the radiation source 1 or the second linear guide (not shown) of the detector 10 parallel to the z-axis in conjunction with rotations, matched to each other, of the detector 10 about the first axis of rotation 11 and of the object slide 20 about the second axis of rotation 21. However, as this is simply a modification of the contrary rotational movements, represented in FIG. 4, of the radiation source 1 and the detector 10 about the virtual point of rotation 33 if object 31 is fixed (this applies only to a rotational laminography, but not in the case of a free movement path), a person skilled in the art can directly transform these movements into movements of the detector 10, the object slide 20 and the radiation source 1 for the X-ray laminography system represented in FIG. 1. It is therefore not necessary to explain in more detail these complex movements which have to be synchronized to each other. As a result, the two contrary rotational movements are converted into sine/cosine projections. For freely defined paths, the transformations to be derived from the geometry can then also be calculated problem-free by a person skilled in the art.

Advantages compared with the X-ray laminography systems known hitherto in the state of the art are achieved by an X-ray laminography system according to the invention. One of these is that, by means of simple, mechanical standard components, an X-ray laminography system according to the invention can be constructed which allows an optional design of linear, rotary or other pattern of movement with regard to the type of error to be detected and orientation of error and, even in the case of fixed high-voltage generators, only those movements of the radiation source 1 that are non-critical for the high-voltage cable are performed.

The linear axes—in the form of the guides 15, 25—are available as standard components, the system concept is thus readily scalable and can be adapted, within broad limits, to the size of objects 31 and imaging components—the radiation source 1 and the detector 10.

The geometric enlargement can be set by varying the distance between the focus of the radiation source 1 and the object 31 as well as the distance between the object 31 and the detector 10, in order that there can be optimization between the size of the area to be inspected and the achievable detail recognition.

The choice of the radiation source 1 corresponds to the scalability of the size; in particular for large objects for examination and those made of strongly absorbent materials, a radiation source 1 can also be used which has a higher capacity than is the case with the rotational laminography systems known from the state of the art, for example a linear accelerator is to be considered here.

A second embodiment example of an X-ray laminography system according to the invention is represented in FIG. 5. This is modified such that a computed tomography procedure (CT procedure) can be carried out with it. For this, the X-ray laminography system known from FIG. 1 is extended by arranging on the object holder 30 a rotary plate 40 which can be rotated by means of a known and not represented CT rotation device about an axis of rotation 41 aligned parallel to the z-axis. In FIG. 5, purely to illustrate that it is the object holder 30, the object 31 according to FIG. 1 is also represented as a dotted line. However, the object that is inspected with this CT system is not arranged directly on the object holder 30, but is fixed on the rotary table 40.

The carrying out of a CT analysis is well known to a person skilled in the art; it therefore does not need to be explained in more detail. The alignment of the individual components of the X-ray laminography system according to FIG. 5 will be discussed only briefly in the following:

The detector 10 is aligned such that it lies in a plane that runs parallel to the xz-plane. The central ray 3 of the radiation source 1 thereby strikes it perpendicularly.

The alignment of the object slide 20 is parallel to the alignment of the detector 10. This is needed only when a displacement of the rotary plate 40 parallel to the x-axis is to be carried out, for example because the object to be examined projects beyond the rotary plate 40 and does not lie completely in the cone of rays 2 of the radiation source 1. The possibility of a precise transverse movement also simplifies the adjustment of the system.

Here too, the distance between radiation source 1 and rotary plate 40 or rotary plate 40 and detector 10 (thus the distance from focus to object or object to detector 10) can be set to the desired image geometry. In addition, also in the case of objects to be examined in z-direction, a synchronous movement of the radiation source 1 along the first linear guide 4 and of the detector 10 along the second linear guide (not shown) parallel to the z-axis can be carried out. Different sections of the object to be examined are thereby inspected in z-direction, wherein a complete CT measurement takes place at each z-height reached. Alternative measurement methods (helical CT, z-scan) are also possible.

With such a second X-ray laminography system according to the invention according to FIG. 5, an X-ray CT scan can also be carried out in addition to the X-ray laminography, with substantially the same system.

Not represented in FIGS. 1 and 5, for reasons of clarity, is a further advantageous development of the invention which provides that the detector can be moved by means of a translation device perpendicular to z, parallel to the sensor plane (thus in the basic position in x-direction). By joining together several individual images taken in different positions, a detector that is wider in this direction can be simulated. In particular the effective sensor surface reduced in the case of large rotation angles, thus the portion of surface facing the radiation source, is thereby effectively enlarged. This translational movement is used in the CT mode to enlarge the measurement circle.

While the invention has been particularly shown and described with reference to preferred embodiments thereof, it will be understood by those skilled in the art that various changes in form and details may be made therein without departing from the spirit and scope of the invention.

LIST OF REFERENCE NUMBERS

1 Radiation source
2 Cone of rays
3 Central ray
4 First linear guide
5 Pivoting axis
10 Detector
11 First axis of rotation
12 First translation device
13 First drive point
14 Second drive point
15 Guide
20 Object slide
21 Second axis of rotation
22 Second translation device
23 Third drive point
24 Fourth drive point
25 Guide
30 Object holder
31 Object
32 Virtual axis of rotation
33 Virtual point of rotation
40 Rotary plate
41 Axis of rotation

What is claimed is:

1. A laminography system comprising:
a first linear guide defining a z-direction of a Cartesian coordinate system;
an imaging radiation source fixable to the first linear guide and movable along the first linear guide, the radiation source configured to form a cone of rays including a central ray defining a y-axis of the Cartesian coordinate system;
a detector disposed in a position so as to be struck at a center thereof by the central ray of the radiation source substantially in an x-direction of the Cartesian coordinate system;
a first rotation device configured to rotate the detector about a first axis of rotation that is parallel to a z-axis of the Cartesian coordinate system and passes through an intersection of the central array and the detector;
a second linear guide, the detector being fixable to the second linear guide and movable on the second linear guide along the first axis of rotation;
an object slide disposed between the radiation source and the detector, the object slide being configured to receive an object for inspection; and
a second rotation device configured to rotate the object slide about a second axis of rotation that is parallel to the first axis of rotation and passes through an intersection of the central ray and the object for inspection.

2. The laminography system recited in claim 1, further comprising an object holder fixable on the object slide and movable relative to the object slide in the x-direction with respect to an alignment of the object slide in an x-z plane.

3. The laminography system recited in claim 1, further comprising at least one of a first translation device configured to move the detector in a y-direction of the Cartesian coordinate system and a second translation system configured to move the object slide in the y-direction.

4. The laminography system recited in claim 1, wherein the first rotation device includes first and second drive points that are independently linearly movable in a y-direction of the Cartesian coordinate system and first and second drive devices that are independently controllable and configured to respectively move the first and second drive points.

5. The laminography system recited in claim 1, wherein the second rotation device includes first and second drive points that are independently linearly movable in a y-direction of the Cartesian coordinate system and first and second drive devices that are independently controllable and configured to respectively move the first and second drive points.

6. The laminography system recited in claim 1, wherein the detector is movable perpendicular to the z-direction and parallel to a plane of the detector.

7. The laminography system recited in claim 1, wherein the imaging radiation source includes a pivoting axis extending in an x-direction of the Cartesian coordinate system and passing through a focus of the imaging radiation source.

8. The laminography system recited in claim 1, further comprising a rotary plate disposed on the object slide and having an axis of rotation aligned with the z-direction, and a CT rotation device configured to drive the rotary plate.

9. The laminography system recited in claim 2, further comprising a rotary plate disposed on the object holder and having an axis of rotation aligned with the z-direction, and a CT rotation device configured to drive the rotary plate.

10. The laminography system recited in claim 4 wherein the first rotation device is configured to also operate as a translation device such that the drive devices translate the detector in a y-direction of the Cartesian coordinate system.

11. The laminography system recited in claim 5, wherein the second rotation device is configured to also operate as a translation device such that the drive devices translate the object slide in a y-direction of the Cartesian coordinate system.

12. The laminography system recited in claim wherein the imaging radiation source is an X-ray source and the detector is an X-ray sensitive detector.

* * * * *